US009865424B2

(12) United States Patent
Ikeda et al.

(10) Patent No.: US 9,865,424 B2
(45) Date of Patent: Jan. 9, 2018

(54) X-RAY INSPECTION SYSTEM

(71) Applicant: System Square Inc., Nagaoka-shi, Niigata (JP)

(72) Inventors: Noriaki Ikeda, Nagaoka (JP); Kazunori Yamada, Nagaoka (JP)

(73) Assignee: SYSTEM SQUARE INC., Nagaoka-Shi (JP)

( * ) Notice: Subject to any disclaimer, the term of this patent is extended or adjusted under 35 U.S.C. 154(b) by 0 days.

(21) Appl. No.: 14/642,736

(22) Filed: Mar. 9, 2015

(65) Prior Publication Data
US 2015/0179391 A1   Jun. 25, 2015

Related U.S. Application Data

(63) Continuation of application No. PCT/JP2012/073301, filed on Sep. 12, 2012.

(51) Int. Cl.
*G01N 23/00* (2006.01)
*H01J 35/16* (2006.01)
*G01N 23/04* (2006.01)
*G01V 5/00* (2006.01)
(Continued)

(52) U.S. Cl.
CPC .............. *H01J 35/16* (2013.01); *G01N 23/04* (2013.01); *G01V 5/0016* (2013.01); *H01J 35/025* (2013.01); *H05G 1/025* (2013.01); *G01N 2223/652* (2013.01); *H01J 2235/127* (2013.01)

(58) Field of Classification Search
CPC ................................ H05G 1/025; G01N 23/04
See application file for complete search history.

(56) References Cited

U.S. PATENT DOCUMENTS

2003/0081730 A1   5/2003  Thandiackal et al.
2006/0140345 A1*  6/2006  Canfield .................. A61B 6/40
                                                                  378/199

FOREIGN PATENT DOCUMENTS

CN       2426273 Y      4/2001
EP       0 426 898 A1   5/1991
JP       07-327973 A    12/1995
(Continued)

OTHER PUBLICATIONS

International Search Report issued in corresponding application PCT/JP2012/073301, pp. 1-2, dated Dec. 18, 2012.
(Continued)

*Primary Examiner* — Dani Fox
(74) *Attorney, Agent, or Firm* — Brinks Gilson & Lione

(57) ABSTRACT

An X-ray inspection system of the present application is capable of blocking the effect of heat from an X-ray source, thereby making it possible to place a heat-sensitive circuit component in the same housing space as the X-ray source. The X-ray inspection system includes a housing 10 provided with an upper housing space 11, in which an X-ray source 32 housed in a cooling container 30 is placed. Due to pressure of a pump 36, a cooling medium circulates between the cooling container 30 and a heat radiating device 33, thereby suppressing the temperature rise of the cooling container 30. Since the cooling container 30 is placed in the upper housing space 11, the upper housing space 11 serves as a cooling space, suppressing the temperature rise. Therefore, heat-sensitive or heat-producing circuit components can be placed in the upper housing space 11.

8 Claims, 4 Drawing Sheets

(51) Int. Cl.
*H01J 35/02* (2006.01)
*H05G 1/02* (2006.01)

(56) References Cited

FOREIGN PATENT DOCUMENTS

| | | |
|---|---|---|
| JP | 11-354288 | 12/1999 |
| JP | 2005-091015 A | 4/2005 |
| JP | 2009-270876 A | 11/2009 |
| JP | 2009-300379 A | 12/2009 |
| JP | 3172652 U | 1/2012 |

OTHER PUBLICATIONS

Japanese Office Action for corresponding Japanese Application No. JP2014-535280 dated Feb. 2, 2016.
Extended European Search Report dated Apr. 19, 2016 for European Application No. 12884488.3, 7 pages.
Office Action dated Oct. 9, 2016 for Chinese Application No. 201280075761.2, 2 pages.

\* cited by examiner

X-RAY INSPECTION SYSTEM

CROSS-REFERENCE TO RELATED APPLICATION

This application is a continuation application of International Application PCT/JP2012/073301, entitled "X-Ray Testing Device", filed on Sep. 12, 2012, the content of which is incorporated herein by reference in its entirety.

TECHNICAL FIELD

The present invention relates to an X-ray inspection system capable of irradiating a work such as a package with X rays for inspecting its package condition or the like, and more particularly, relates to an X-ray inspection system capable of effectively cooling an X-ray source and also suppressing the temperature rise of circuit components.

RELATED ART

In an X-ray inspection system disclosed in Patent Literature 1: Japanese Unexamined Patent Application Publication No. 2005-91015, an X-ray generator is placed in an upper part of a main body of the system. The X-ray generator is configured such that an insulating oil is contained in a metal box and an X-ray tube is housed therein in an immersed state. Beneath the X-ray generator, an X-ray detector is provided for detection of X rays.

When an object to be inspected passes through a space between the X-ray generator and the X-ray detector, X rays emitted from the X-ray generator are applied to the object to be inspected. X rays transmitted through the object to be inspected are detected by the X-ray detector, and a content of the object to be inspected, which is in a package, is recognized in a gray image, making it possible to determine whether a foreign body is present or not.

In a foreign body detection system disclosed in Patent Literature 2: Japanese Unexamined Patent Application Publication No. 2009-270876, a concealing box covering an X-ray irradiation part equipped with an X-ray tube is reclosably placed at an upper part of a housing, and the concealing box has lead-in and lead-out openings each equipped with a fan. Inside the concealing box, a partition is provided such that a lead-in side passage from the lead-in opening to the X-ray irradiation part is separated from a lead-out side passage from the X-ray irradiation part to the lead-out opening.

Inside the concealing box, moreover, a control board is placed at a top, bottom or side of the concealing box such that an air flow between the lead-in side passage and the lead-out side passage is prevented from being blocked by the presence of the control board.

SUMMARY OF THE INVENTION

Technical Problem

Since the X-ray tube of the X-ray generator is left with a function as a heat source, a considerably large amount of heat is emitted from the box housing the X-ray tube, greatly increasing the temperature in the internal space of the system's main body in which the X-ray generator is placed. If a circuit board is placed near the X-ray generator, circuit components mounted on the circuit board easily suffer from the heat. For example, when the circuit component is a CPU, there is a risk of malfunction due to heat; when the circuit component is an AC/DC converter, there is a likelihood that the converted DC output power will decrease disadvantageously. Therefore, the installation location of the circuit board is limited.

In the X-ray generator disclosed in Patent Literature 1, a display unit is placed near the X-ray generator, but in consideration of the effect of the heat emitted from the X-ray generator, a display driving circuit for driving the display unit should be located apart from the display unit, making it difficult to stabilize the display operation of the display unit.

In Patent Literature 2, on the other hand, air is introduced into the concealing box from the outside so that the X-ray irradiation part can be cooled by an air flow inside the concealing box.

However, since the air is introduced into the concealing box from the outside, there is a likelihood that dust entering the concealing box along with the outside air will adhere to the control board, causing problems such as short circuit in the control board. In addition, the foreign body detection system may be installed in a high-temperature or high-humidity workplace or a workplace in which chemicals such as chlorine are used; in this case, the temperature inside the concealing box cannot be reduced sufficiently, and moisture or chemical components may easily be introduced into the concealing box and helps the dust to adhere to the control board, causing the failure of the control circuit.

Moreover, since the control board is located at a position where the control board does not interfere with the air flow between the lead-in side passage and the lead-out side passage inside the concealing box, the installation location of the control board is limited, which, for example, makes it difficult to locate the display unit driving circuit close to the display unit.

The present invention is to solve the above-mentioned problem in the prior art and has an object to provide an X-ray inspection system capable of effectively cooling an X-ray tube served as an X-ray source and also capable of effectively suppressing the temperature rise of circuit components disposed around the X-ray source.

Solution to Problem

In an X-ray inspection system comprising a work passage, an X-ray source provided at one side of the work passage, and an X-ray detection sensor provided at the other side thereof, the present invention is characterized by further including a cooling container housing the X-ray source, a heat radiating device, a conduit connecting the inside of the cooling container and the heat radiating device, and a pump for circulating a cooling medium between the inside of the cooling container and the heat radiating device through the conduit, the cooling container being placed in an upper housing space inside a housing, the heat radiating device being placed outside the upper housing space, a circuit component of an electric circuit being placed in the upper housing space along with the cooling container.

In the X-ray inspection system according to the present invention, the cooling container housing the X-ray source can be cooled by the circulating cooling medium, and heat emitted from the X-ray source can be released into the outside air through the heat radiating device located outside the upper housing space. This makes it possible to effectively cool the cooling container housing the X-ray source and suppress the temperature rise in the upper housing space in which the cooling container is placed.

Since the temperature rise can be suppressed in the upper housing space, even if various types of circuit components are disposed in the same upper housing space along with the cooling container, the temperature rise of various types of circuit components can be suppressed. In the case of a circuit component for a heat-producing circuit such as a power supply, moreover, since this circuit component is placed in the upper housing space, it can be expected that heat emitted from the circuit component will be dissipated by the cooling container lying in the same space.

In the present invention, the upper housing space may be formed inside an upper openable part of the housing such that the upper housing space is secluded and sealed off from the outside as the upper openable part is closed.

Since the upper housing space can be sealed off by closing the upper openable part of the housing, the temperature rise can be effectively suppressed in the upper housing space in which the cooling container is placed.

In the present invention, moreover, a lower housing space communicating with the upper housing space may be placed below the upper housing space, and another circuit component may be placed in the lower housing space.

In this case, a heat-producing circuit component may be placed in at least either the upper housing space or the lower housing space.

If another circuit component, particularly, a heat-producing circuit component is placed in the upper housing space or the lower housing space communicating therewith, heat emitted from the heat-producing circuit component will be applied to the upper housing space. Then, since the cooling container capable of serving as a cooling device exists in the upper housing space, the heat can easily be transferred to the outside by the cooling medium, suppressing the temperature rise not only in the upper housing space but also in the lower housing space. Therefore, heat-sensitive circuit components disposed in the upper housing space or the lower hosing space can be protected from the heat.

It should be noted that in the present invention, the upper openable part can be locked by a locking mechanism capable of being released only when unlocking operation is performed from the outside.

In the present invention, a display unit may be attached to the upper openable part such that the display unit comes close to and faces the cooling container as the upper openable part is closed.

Furthermore, a circuit component of a driving circuit for driving the display unit may be placed in the upper housing space.

According to the present invention, even if the display unit is placed near the X-ray source, extraordinary temperature rise around the display unit can be prevented by the cooling medium circulating through the cooling container. Moreover, since the temperature rise of the display unit driving circuit can also be suppressed, the driving circuit can be placed near the display unit, so that deterioration in the quality of information display by the display unit can be prevented.

In the present invention, preferably, the sensor is placed in a sensor housing space, and the sensor housing space communicates with the upper housing space.

If the sensor is placed in the sensor housing space communicating with the upper housing space, heat emitted from the sensor can easily be transferred to the upper housing space. Then, since the cooling container capable of serving as a cooling device exists in the upper housing space, the heat emitted from the sensor can easily be transferred to the outside by the cooling medium.

Advantageous Effects of Invention

According to the present invention, since the cooling container housing the X-ray source is cooled by the cooling medium, the temperature rise can be suppressed in the upper housing space in which the cooling container is placed. Therefore, even though a circuit component is placed in the upper housing space, the circuit component can be effectively prevented from being affected by heat. In addition, since heat emitted from the circuit component can also be dissipated by the cooling container lying in the same space, the temperature rise due to the heat emitted from the circuit component can also be suppressed.

DETAILED DESCRIPTION OF EMBODIMENTS

Figure 1:
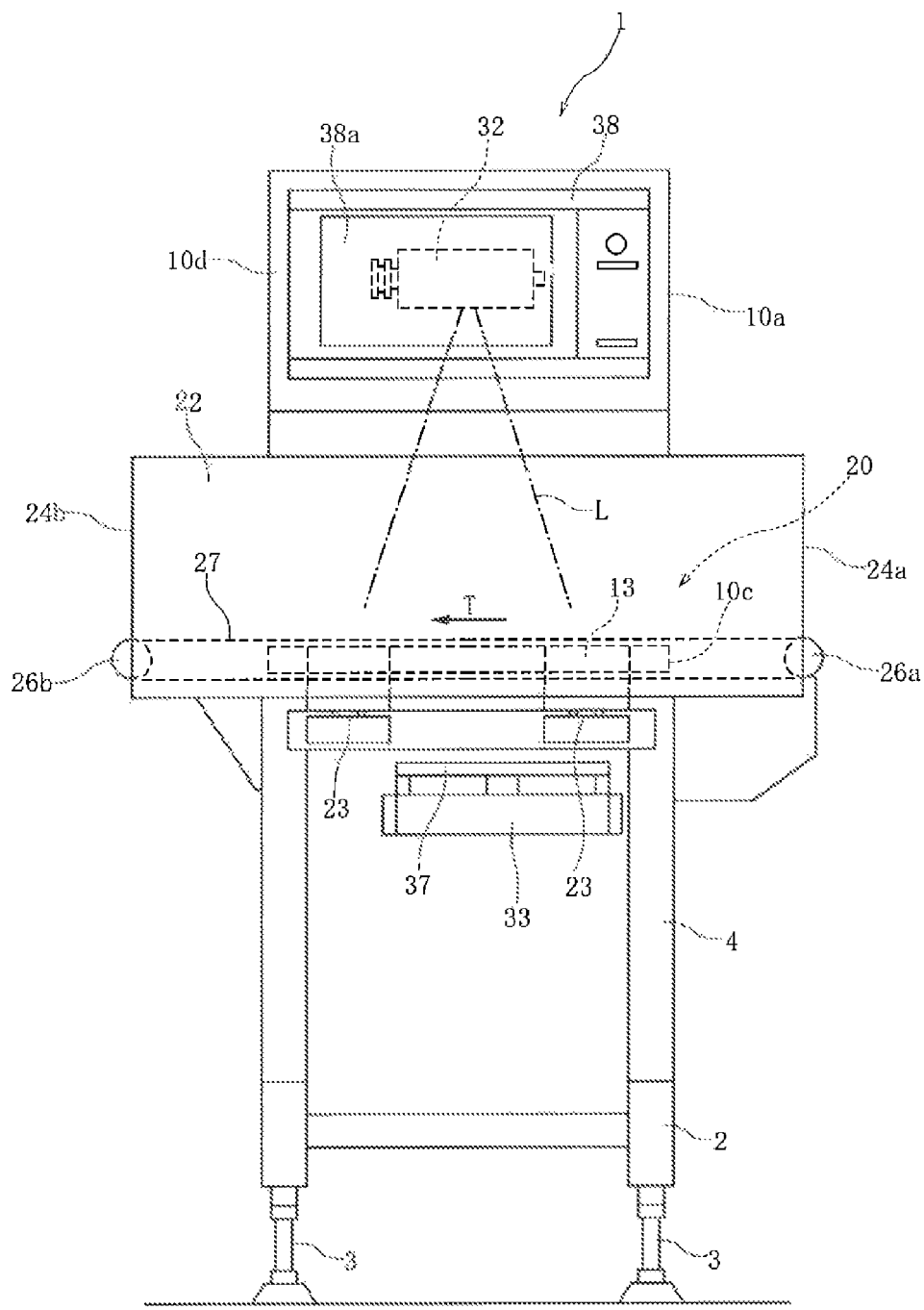
FIG. 1 is a front view of an X-ray inspection system according to an embodiment of the present invention.
Figure 2:
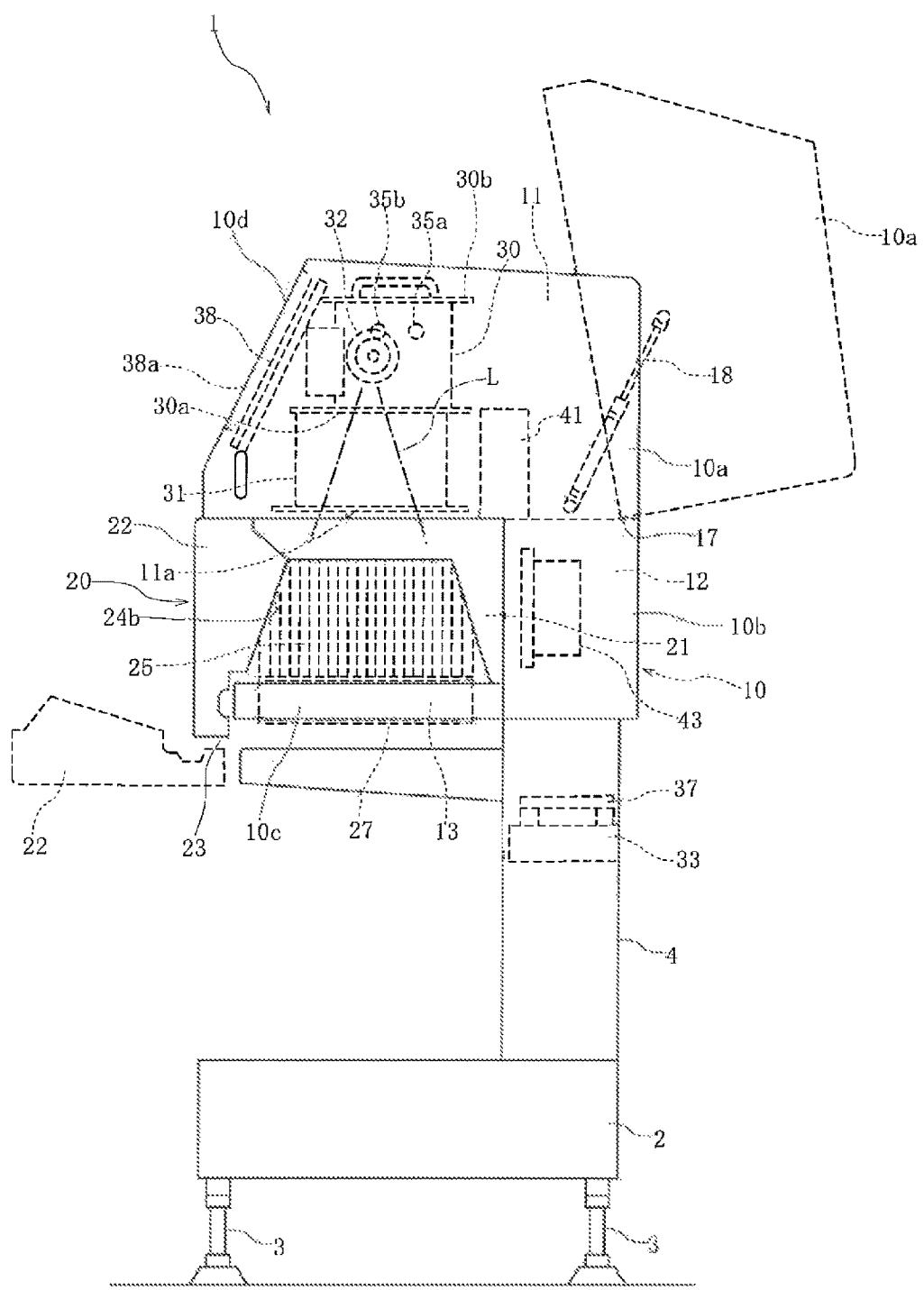
FIG. 2 is a right side view of the X-ray inspection system.

As shown in FIGS. 1 and 2, an X-ray inspection system 1 according to an embodiment of the present invention is installed on a work base with legs 3 attached to a lower frame 2. A support frame 4 is provided above the lower frame 2, and a housing 10 is fixed on and supported by the support frame 4. The lower frame 2, the support frame 4 and the housing 10 are formed of a metal plate.

Figure 3:
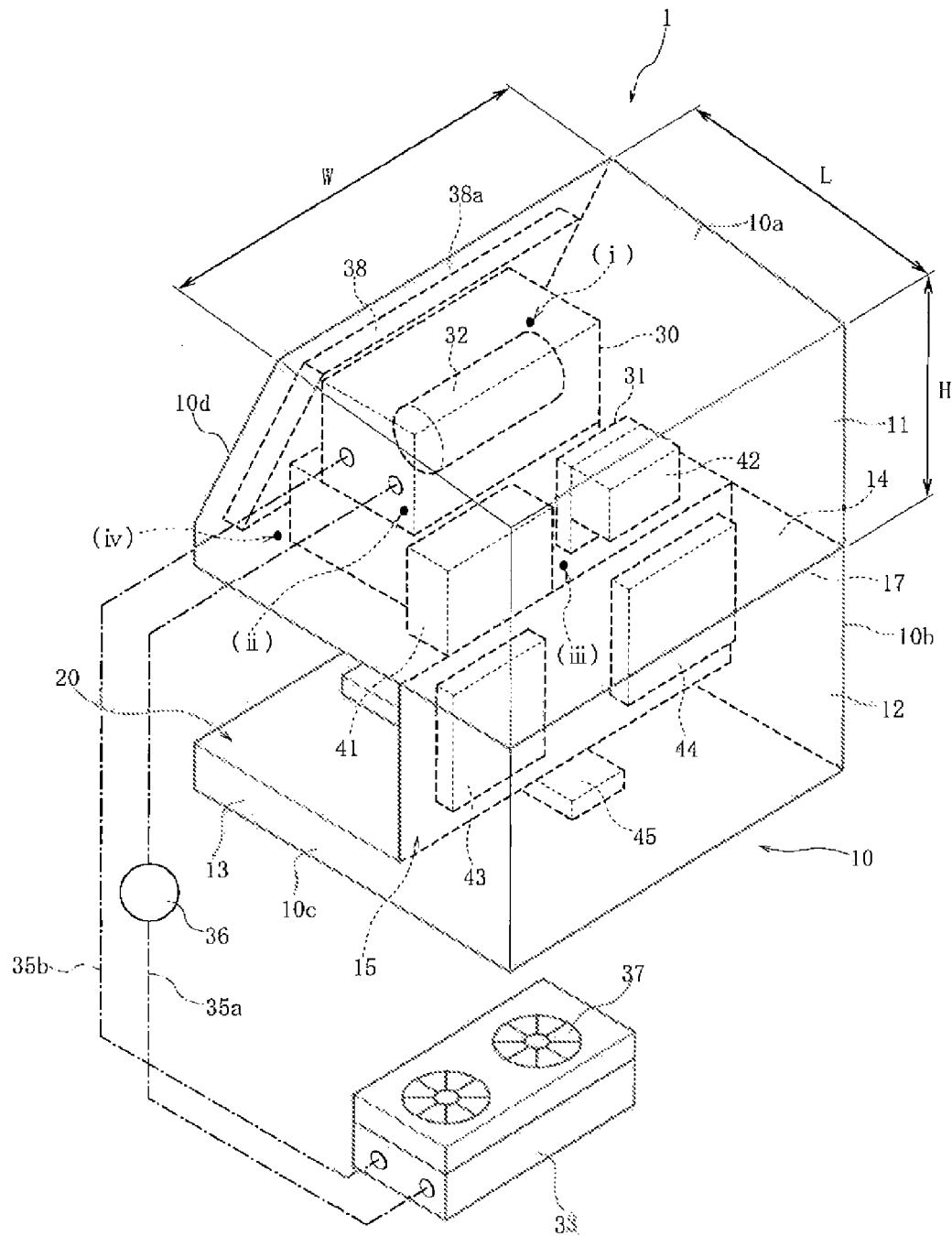
FIG. 3 is a perspective view showing the positional relationship between an upper housing space, a lower housing space and a sensor housing space formed inside a housing, as seen from the rear side of the X-ray inspection system.

As shown in FIGS. 2 and 3, the housing 10 has an upper openable part 10*a*, a lower fixed part 10*b* and an extension 10*c* extending forward from the lower fixed part 10*b*. The internal space of the upper openable part 10*a* is referred to as upper housing space 11, the internal space of the lower fixed part 10*b* is referred to as lower housing space 12, and the internal space of the extension 10*c* is referred to as sensor housing space 13. The upper housing space 11 and the lower housing space 12 communicate with each other through a passage 14, and the lower housing space 12 and the sensor housing space 13 communicate with each other through a passage 15.

Between the upper openable part 10*a* and the lower fixed part 10*b*, a hinge 17 is provided such that the upper openable part 10*a* can turn between a closed position indicated by solid line in FIG. 2 and an open position indicated by dotted line in FIG. 2 with the hinge 17 acting as a pivot. It should be noted that at the hinge 17, a hinge mechanism is provided between a metal plate forming the upper openable part 10*a* and a metal plate forming the lower fixed part 10*b*, but the hinge mechanism is omitted from the drawings.

As shown in FIG. 2, a stopper mechanism 18 is provided between the upper end of the lower fixed part 10*b* and the upper openable part 10*a*, enabling the upper openable part 10*a* to stay stably in the open position shown in FIG. 2.

With the upper openable part 10*a* put in the closed position, as indicated by solid line in FIG. 2, the upper openable part 10*a* can be locked by a locking mechanism capable of being released only when unlocking operation is performed from the outside. This locking mechanism may be screwing. The locking mechanism is released only when needed for maintenance or the like, and the upper openable part 10*a* is turned to the open position so that each of various components disposed in the upper housing space 11 can be replaced or repaired.

When the upper openable part 10a is in the closed position, the upper housing space 11 is secluded and sealed off from the outside except for the passage 14 to the lower housing space 12. The lower housing space 12 is sealed off except for the passage 14 to the upper housing space 11 and the passage 15 to the sensor housing space 13, and the sensor housing space 13 is also sealed off except for the passage 15 to the lower housing space 12.

In this specification, when referred to "sealed off" of the upper housing space 11, the lower housing space 12 and the sensor housing space 13, the sealed off means that the spaces thereabove are structurally secluded from the outside air by the metal plates forming the housing 10, not leaving any passage which purposefully facilitates air inflow from or outflow to the outside. Therefore, a small gap may be left at a part where the edges of the metal plates overlap each other, or a small gap may be left between the upper openable part 10a, which can be opened or closed, and the lower fixed part 10b, or a minimum hole may be provided for leading wires out of the housing.

At the passage 14, an opening is provided for communication between the upper housing space 11 and the lower housing space 12; at the passage 15, an opening is provided for communication between the lower housing space 12 and the sensor housing space 13.

A work passage 20 is formed between the upper openable part 10a and the extension 10c of the housing 10. As shown in FIG. 2, the work passage 20 has a fixed cover 21 at its rear side and an openable cover 22 at its front side. The fixed cover 21 is fixed to the front side of the lower fixed part 10b of the housing 10.

Through a hinge shown in FIG. 1, the lower end of the openable cover 22 is pivotably connected to the front end of the extension 10c of the housing 10. The openable cover 22 can turn between a closed position indicated by solid line in FIG. 2 and a forwardly turned, open position indicated by dotted line.

As shown in FIG. 2, when the openable cover 22 is put in the closed position, an inlet 24a is formed between the fixed cover 21 and the openable cover 22. As shown in FIG. 1, an outlet 24b is formed at the side opposite to the inlet 24a. As shown in FIG. 2, the inlet 24a is provided with a lead-containing, X-ray shielding sheet 25, and the outlet 24b is also provided with another X-ray shielding sheet 25. The X-ray shielding sheet 25 has vertically extending cut lines at regular intervals, allowing the passage of the work.

In the work passage 20, as shown in FIG. 1, a roller 26a is provided below the inlet 24a, and a roller 26b is provided below the outlet 24b. One of the rollers 26a and 26b is a driving roller, while the other is a driven roller. A conveyor belt 27 is stretched between the rollers 26a and 26b. As shown in FIGS. 1 and 2, the extension 10c of the housing 10 is located between vertically opposed two separate parts of the conveyor belt 27.

A cooling container 30 is placed in the upper housing space 11 inside the upper openable part 10a, and an X-ray source 32 is housed in the cooling container 30. The X-ray source is an X-ray tube housing a target for generating X rays and an electrode for letting electrons collide with the target inside a glass tube. The cooling container 30 is formed of a metal material that can block X rays but transmit heat, sealed off, and fixed on a support 31 placed at the bottom of the upper openable part 10a.

As shown in FIGS. 1 and 2, a heat radiating device 33 is supported by the support frame 4. The heat radiating device 33 is a radiator. As shown in FIG. 3, the inside of the cooling container 30 and the inside of the heat radiating device 33 are connected to each other through circulation conduits 35a and 35b, and a pump 36 is placed in the middle of the circulation conduit 35a. Owing to the transfer force of the pump 36, a cooling medium can be circulated between the cooling container 30 and the heat radiating device 33 through the circulation conduits 35a and 35b. As the cooling medium, an insulating oil having excellent electrical insulation and high thermal conductivity can be employed.

As shown in FIG. 3, the cooling container 30 is placed in the upper housing space 11, while the heat radiating device 33 is placed outside the upper housing space 11, more specifically, fixed to the support frame 4 outside the housing 10. Moreover, the support frame 4 is provided with a cooling fan 37 for facilitating air circulation around the heat radiating device 33.

Between the upper housing space 11 and the underlying work passage 20, a metal plate and a filter put in a window of the metal pale are provided so as to separate the upper housing space 11 and the space of the work passage 20. FIGS. 2 and 3 show an area L that can be irradiated with X rays emitted from the X-ray source 32. The X rays emitted downwardly from the X-ray source 32 passes through the internal space of the support 31, transmits through the filter located at the bottom 11a of the upper housing space 11 and is then applied to the underlying work passage 20.

As shown in FIGS. 1 to 3, the front part 10d of the upper openable part 10a of the housing 10 is inclined, and a display unit 38 is mounted on the front part 10d. As shown in FIG. 1, the display unit 38 has a display screen 38a that can be seen from the front. The display screen 38a may be provided with a color liquid crystal panel or the like.

As shown in FIGS. 2 and 3, the display unit 38 faces the cooling container 30 inside the upper housing space 11, and the display unit 38 is located close to the cooling container 30.

As shown in FIG. 3, first and second circuits 41 and 42 are provided in the upper housing space 11. The first circuit 41 has a motherboard mounted with circuit components of a driving circuit for operating a CPU or the display unit 38 or the like. The second circuit 42 has a circuit board mounted with circuit components constituting a switched-mode power supply, i.e., an AC/DC converter. In FIG. 3, the first and second circuits 41 and 42 are located behind the support 31 supporting the cooling container 30, but these circuits may be located in front of the support 31 (on the opposite side across the support 31 in FIG. 3) or at right and left sides of the support 31 (at front and rear sides as seen in FIG. 2).

As shown in FIG. 3, third and fourth circuits 43 and 44 are provided in the lower housing space 12 of the housing 10. These circuits 43 and 44 have a circuit board mounted with circuit components constituting an inverter.

An X-ray sensor 45 is provided in the sensor housing space 13 inside the extension 13 of the housing 10. The X-ray sensor 45 is a line sensor facing the lower side of the X-ray source 32 across the work passage 20.

During the inspection with the X-ray inspection system 1, the rollers 26a and 26b rotate to make the conveyor belt 27 circle around in the counterclockwise direction (T direction) in FIG. 1. A work such as a package housing a food in a bag is delivered to the conveyor belt 27, conveyed to the work passage 20 through the inlet 24a by the conveying force of the conveyor belt 27, and then brought out of the outlet 24b.

At the work passage 20, X rays emitted from the X-ray source 32 are applied to the work, and X rays transmitted through the work are detected by the X-ray sensor 45 to obtain an image of the work such as a package, so that whether a foreign body is present or not can be checked based on the image.

During the inspection, the X-ray source 32 continuously emits heat. Its heating value is about 100 to 500 Wh (watt-hour). Since the cooling medium is circulating through the cooling container 30, the heat emitted from the X-ray source 32 is conveyed by the cooling medium, transferred to the heat radiating device 33 through the circulation conduits 35a and 35b, and released to the outside of the housing 10 through the heat radiating device 33.

Since the temperature rise of the cooling container 30 can be suppressed by the circulation of the cooling medium, the temperature rise can also be suppressed in the upper housing space 11 in which the cooling container 30 is placed. Therefore, even if relatively heat-sensitive circuit components constituting a CPU, AC/DC converter or the like are disposed in the upper housing space 11, these circuit components can be prevented from being placed in a high-temperature environment. This prevents malfunction of the CPU or reduction in conversion efficiency of the AC/DC converter.

The display unit 38 is located close to the cooling device 30 at a position facing the cooling container 30, and since the cooling container 30 is controlled such that the temperature will not rise because of the circulation of the cooling medium, the display unit 38 can be prevented from being heated by the heat emitted from the X-ray source 32. With the cooling medium circulating through the cooling container 30, moreover, heat emitted from the display unit 38 can be released into the outside air through the heat radiating device 33.

Furthermore, since the cooling container 30 is placed in the upper housing space 11 so as to suppress the temperature rise therein, the driving circuit for the display unit can be located around the cooling container 30 and close to the display unit 38. Since the driving circuit can be located close to the display unit 38, the display quality of the display unit 38 can be stabilized.

In the case where the first circuit 41 or the second circuit 42 placed in the upper housing space 11 includes a heat-producing circuit component, heat emitted from such a circuit component will be dissipated into the upper housing space 11. However, since the cooling container 30 cooled by the circulating cooling medium exists in the upper housing space 11, the temperature rise can be suppressed in the upper housing space 11, even though the heat is emitted from the circuit component.

That is, the cooling container 30 serves as a kind of cooling device in the upper housing space 11, so that the upper housing space 11 becomes a cooling space. Therefore, even though the heat-producing circuit component is placed in the upper housing space 11, the excessive temperature rise in the upper housing space 11 can be prevented.

As shown in FIG. 3, the third and fourth circuits 43 and 44 are placed in the lower housing space 12. When these circuits include a heat-producing circuit component, emitted heat transmits upwardly within the housing 10 and reaches the upper housing space 11. In addition, heat from the X-ray sensor 45 and its peripheral circuit also reaches the upper housing space 11 via the lower housing space 12. For this heat, the upper housing space 11 also serves as a cooling space, preventing the excessive temperature rise in the upper housing space 11.

The temperature rise in the upper housing space 11 is suppressed by the presence of the cooling container 30, but it is still impossible to avoid causing temperature gradient in the upper housing space 11, so that the temperature becomes relatively high in the upper part of the upper housing space 11 and relatively low in the lower part. Therefore, circuit components mounted on the uppermost part of the first and second circuits 41 and 42 are preferably located at the same level as or below the upper surface 30b of the cooling container 30 cooling the upper housing space 11. More preferably, the circuit components are placed in a space below the bottom 30a of the cooling container 30.

That is, at least heat-sensitive circuit components among a plurality of sets of circuit components placed in the upper housing space 11, i.e., at least some of the circuit components may be located below the upper surface 30b of the cooling container 30 serving as a cooling device, and preferably, below the bottom 30a, whereby the heat-sensitive circuit components can easily be prevented from being exposed to high temperature.

Figure 4:
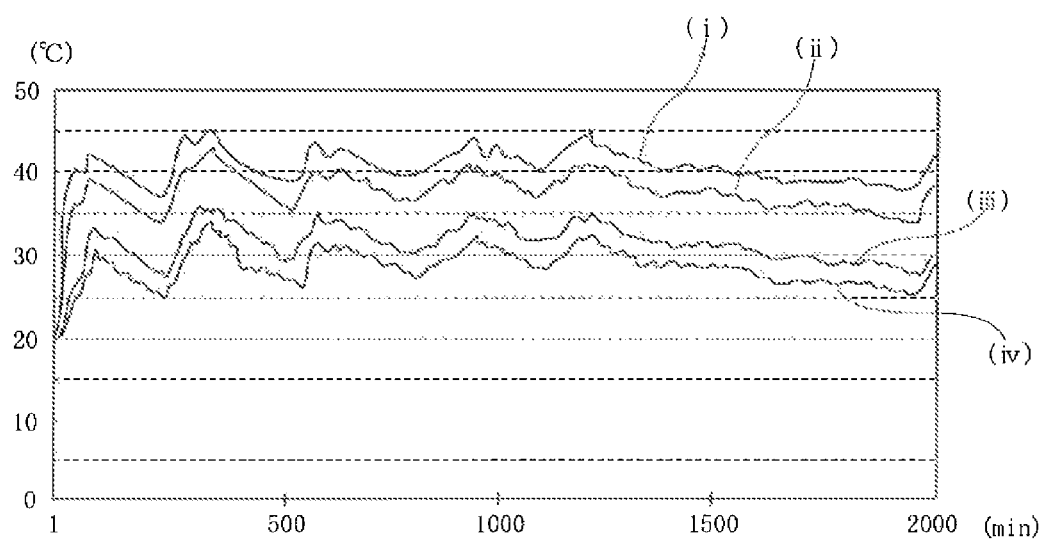
FIG. 4 is a diagram showing measurement results of temperature inside the upper housing space.

FIG. 4 shows temperature changes measured at a several points in the upper housing space 11 during the operation of the X-ray source 32.

In the upper housing space 11 of the X-ray inspection system 1 used for measurement, the height H shown in FIG. 3 was 320 mm, the front-to-rear length L was 550 mm, and the width W was 458 mm. As shown in FIG. 3, the temperature measurement points include a point (i) above the cooling container 30, a point (ii) near the bottom 30a of the cooling container 30, a point (iii) at the rear part of the bottom of the upper housing space 11, and a point (iv) at the front part of the bottom of the upper housing space 11.

In FIG. 4, the ordinate represents temperature (° C.), while the abscissa represents operating elapsed time (minute), and temperature changes measured at the individual points (i), (ii), (iii) and (iv) are shown in the graph.

As shown in FIG. 4, since the cooling container 30 is placed in the upper housing space 11, the temperature rise can be suppressed in the upper housing space 11, limiting the maximum temperature to about 45° C. Particularly, the temperature can be limited to 35° C. or less at a position below the bottom 30a of the cooling container 30, so that this place is suitable for the location of heat-sensitive circuit components.

REFERENCE SIGNS LIST

1 X-ray Inspection System
10 Housing
10a Upper Openable Part
10b Lower Fixed Part
10c Extension
11 Upper Housing Space
12 Lower Housing Space
13 Sensor Housing Space
20 Work Passage
30 Cooling Container
30b Upper Surface of Cooling Container
31 Support
32 X-ray Source
33 Heat Radiating Device
35a, 35b Circulation Conduit
36 Pump
41, 42, 43, 44 Circuit
45 X-ray Sensor

The invention claimed is:
1. An X-ray inspection system comprising:
a work passage;
an X-ray source provided at one side of the work passage;

an X-ray detection sensor provided at the other side thereof;
a cooling container housing the X-ray source;
a heat radiating device;
a tubing connecting to the inside of the cooling container and the heat radiating device;
a pump for circulating liquid cooling medium between the inside of the cooling container and the heat radiating device through the tubing, the cooling container being placed inside an upper housing, the heat radiating device which is mounted apart from the X-ray source and is located outside the upper housing; and
a circuit component of an electric circuit being placed in the upper housing along with the cooling container,
wherein the liquid cooling medium in the tubing is supplied to the cooling container to suppress a temperature rise of the cooling container housing the X-ray source, and the cooling container serves as a cooling device to suppress a temperature rise both to the upper housing and to the circuit component.

2. The X-ray inspection system according to claim 1, wherein the upper housing is formed inside an upper openable part of the housing such that the upper housing is secluded and sealed off from the outside when the upper openable part is closed.

3. The X-ray inspection system according to claim 2, wherein a lower housing communicating with the upper housing is placed below the upper housing, and another circuit component is placed in the lower housing.

4. The X-ray inspection system according to claim 2, wherein a heat-producing circuit component is placed in at least either the upper housing or the lower housing.

5. The X-ray inspection system according to claim 2, wherein the upper openable part is locked by a locking mechanism capable of being released only when unlocking operation is performed from the outside.

6. The X-ray inspection system according to claim 2, wherein a display unit is attached to the upper openable part such that the display unit comes closer to and faces the cooling container as the upper openable part is closed.

7. The X-ray inspection system according to claim 6, wherein a circuit component of a driving circuit for driving the display unit is placed in the upper housing.

8. The X-ray inspection system according to claim 1, wherein the sensor is placed in a sensor housing, and the sensor housing communicates with the upper housing.

* * * * *